United States Patent
Weston et al.

(10) Patent No.: US 12,374,459 B2
(45) Date of Patent: Jul. 29, 2025

(54) METHOD OF EVALUATING TEXT SIMILARITY FOR DIAGNOSIS OR MONITORING OF A HEALTH CONDITION

(71) Applicant: Novoic Ltd., London (GB)

(72) Inventors: Jack Weston, Greater London (GB); Emil Fristed, Greater London (GB)

(73) Assignee: Novoic Ltd., London (GB)

(*) Notice: Subject to any disclaimer, the term of this patent is extended or adjusted under 35 U.S.C. 154(b) by 1048 days.

(21) Appl. No.: 17/377,612

(22) Filed: Jul. 16, 2021

(65) Prior Publication Data
US 2023/0034401 A1 Feb. 2, 2023

(51) Int. Cl.
*G16H 50/20* (2018.01)
*G06F 40/166* (2020.01)
*G06F 40/284* (2020.01)
*G06F 40/30* (2020.01)
*G06N 20/00* (2019.01)
(Continued)

(52) U.S. Cl.
CPC ........... *G16H 50/20* (2018.01); *G06F 40/166* (2020.01); *G06F 40/284* (2020.01); *G06F 40/30* (2020.01); *G06N 20/00* (2019.01); *G16H 10/60* (2018.01); *G16H 50/70* (2018.01)

(58) Field of Classification Search
CPC ........ G16H 50/20; G16H 10/60; G16H 50/70; G06F 40/166; G06F 40/284; G06F 40/30; G06N 20/00; G06N 3/0455; G06N 3/082; G06N 3/0895; G06N 3/096
See application file for complete search history.

(56) References Cited

U.S. PATENT DOCUMENTS

2020/0327882 A1* 10/2020 Vairavan ............... G10L 15/063
2021/0182489 A1*  6/2021 Barkan .................... G06N 3/08
2021/0225518 A1*  7/2021 Papp .................... A61B 5/7475
(Continued)

OTHER PUBLICATIONS

Devlin et al., "Bert: Pre-training of deep bidirectional transformers for language understanding." arXiv preprint arXiv:1810.04805 (2018). 16 pages.

(Continued)

*Primary Examiner* — Stella L. Woo
(74) *Attorney, Agent, or Firm* — Smith Baluch LLP

(57) ABSTRACT

The invention relates to a computer implemented method of training a machine learning model to evaluate the similarity of a candidate text to a reference text for determining or monitoring a health condition, where the model takes a text comparison pair comprising a reference text and a candidate text, each comprising data encoding a text sequence, the method comprising: pre-training an edit encoder to learn to generate an edit-space representation of an input text comparison pair, where the edit-space representation encodes information for mapping the reference text to the candidate text, the edit encoder comprising a machine learning model; and performing task-specific training by adding a task-specific network layer and training the task-specific network layer to map an edit-space representation generated by the pre-trained edit encoder to an output associated with a health condition. Edit-space representations learned in this way are able to encode a greater range of changes in language use than known metrics used to evaluate machine translations.

18 Claims, 5 Drawing Sheets

(51) Int. Cl.
    *G16H 10/60*     (2018.01)
    *G16H 50/70*     (2018.01)

(56) References Cited

U.S. PATENT DOCUMENTS

2021/0312942 A1* 10/2021 Rudzicz ............... A61B 5/4803
2022/0108714 A1* 4/2022 Novikova ............... G10L 15/02
2022/0284049 A1* 9/2022 Christensen ........ G06F 16/3323

OTHER PUBLICATIONS

Jelinek et al., "Perplexity—a measure of the difficulty of speech recognition tasks." The Journal of the Acoustical Society of America 62.S1 (1977): S63-S63. 2 pages.

Liu et al., "Roberta: A robustly optimized bert pretraining approach." arXiv preprint arXiv:1907.11692 (2019). 13 pages.

Sellam et al., "BLEURT: Learning robust metrics for text generation." arXiv preprint arXiv:2004.04696 (2020). 12 pages.

Tiedemann, "Bitext alignment." Synthesis Lectures on Human Language Technologies 4.2 (2011). Abstract. 2 pages.

Vaswani et al., "Attention is all you need." Advances in neural information processing systems. 2017. 11 pages.

Wieting et al., "ParaNMT-50M: Pushing the limits of paraphrastic sentence embeddings with millions of machine translations." arXiv preprint arXiv:1711.05732 (2017). 15 pages.

Zhang et al., "Bertscore: Evaluating text generation with bert." arXiv preprint arXiv:1904.09675 (2019). 43 pages.

Zhao et al., "Moverscore: Text generation evaluating with contextualized embeddings and earth mover distance." arXiv preprint arXiv:1909.02622 (2019). 16 pages.

\* cited by examiner

METHOD OF EVALUATING TEXT SIMILARITY FOR DIAGNOSIS OR MONITORING OF A HEALTH CONDITION

TECHNICAL FIELD

The present invention relates to computer-implemented methods and systems for training a machine learning model to evaluate the similarity of text, in particular to determine and/or monitor a health condition. The invention also relates to applying the trained machine learning model to speech transcripts in order to monitor and/or diagnose a health condition, and a system or diagnostic tool incorporating the trained model.

BACKGROUND

Alzheimer's disease (AD) has been described as having a "silent" phase of disease progression, occurring up to 20 years before clinical dementia can be formally diagnosed. Evidence suggests that one of the earliest cognitive changes in Alzheimer's disease is in declarative memory, specifically in episodic memory, likely caused by the accumulation of Alzheimer's pathology in the hippocampus. Further evidence from neuroimaging research have also reported increased atrophy of the hippocampus in early AD, associated with episodic memory impairment, long before a formal diagnosis of clinical dementia.

By age 50, approximately one in ten people will have Alzheimer's pathology. An ageing population means the number living with the disease and the associated pressure on health services will only increase. This motivates the need to identify AD at an earlier stage so that it can be better treated and managed before more debilitating symptoms develop.

Current tests for AD are either not sensitive to changes at the earlier disease stages or are too costly or impractical to implement. Clinical trials targeting the earliest stages of the disease typically rely on measuring amyloid Aβ biomarkers using positron emission tomography or in cerebrospinal fluid obtained from lumbar puncture. However, the high cost, invasive nature, and need for specialist equipment and medical staff for these procedures, restricts use in standard clinical care and broader population screening. New blood plasma biomarkers also hold promise for reducing screening costs, but remain invasive, have associated laboratory costs, currently show significant variability between methods and laboratories, and do not differentiate between different clinical stages of the disease.

Another approach considers the use of cognitive composites, comprising a range of measures sensitive to disease-related impairments, to track Aβ-related decline. Episodic memory has been identified as a key early change in these composites.

The traditional way of measuring episodic memory impairment is using a story recall task such as the Wechsler Logical Memory Delayed Recall (LMDR) test. In this task the participants to be assessed are told a story and then asked to repeat it: sometimes immediately, sometimes after a delay. The test is scored by quantifying how much of the information from the story that was retained in the retelling. This is typically done by manual scoring, where the person who scores the test has a list of "story elements", and the person being tested will be awarded points for each element they recall.

Given that such cognitive tests and composites typically require a significant amount of qualified staff time to administer and score, there have been recent attempts to automate these tests. Generally, these have been focussed on computer implemented methods of aligning and comparing the retelling to the list of manually defined elements, before computing the standard scoring metric.

Such methods suffer from a number of problems. Most significantly, basing the metric on differences in a manually defined list of elements means these measures miss other patterns of differences between the reference story and the story retelling. A simple example is that remembering certain parts of the story could be more indicative of AD than other parts. More fundamentally, the range of cognitive impairments associated with early stage AD has been shown to have a wider range of effects on speech and memory, including episodic memory resulting in more vague retelling, semantic memory resulting in less semantic diversity and language production resulting in more improbable sentences. Existing metrics, generally based on discrepancies between story elements, therefore miss a wide range of more subtle differences that are indicative of early stage AD.

Accordingly there exists a need for a metric for comparing the similarity between a reference text and a recalled version of the text that captures this range of subtle signals. Such a measure would not only be applicable to AD but to any health condition which resulted in changes in a recalled version of a reference text. Similarly, this kind of metric would also be applicable where an appropriate reference can be constructed for a different task (e.g. for a picture description task a reference could be a description containing all elements of the picture)—to compare the similarity of the speech of someone with unknown medical status to the speech of others where associated clinical characteristics are known (e.g. whether the speech is closer to a reference of AD speech or to a reference of healthy speech). Speech changes are observed across a wide range of neurodegenerative and psychiatric conditions and so there is broad scope for applying such a measure to identifying and monitoring a wide range of conditions.

The present invention aims to solve one or more of the challenges described above, and in particular enable improved early detection and quantifiable monitoring of a health condition, such as Alzheimer's disease. Although primarily directed at the detection and monitoring of health conditions that may affect speech, it is noted that such a solution would also find application in a wide range of other fields, where computing a more "human" assessment of the similarity of a candidate text and a reference text is required.

SUMMARY

In a first aspect of the invention there is provided a computer implemented method of training a machine learning model to evaluate the similarity of a candidate text to a reference text for determining or monitoring a health condition, where the machine learning model takes as input a text comparison pair, where a text comparison pair comprises a reference text and a candidate text, each comprising data encoding a text sequence, the method comprising: pre-training an edit encoder to learn an edit-space representation of a text comparison pair, where the edit-space representation encodes information for mapping the reference text to the candidate text, the edit encoder comprising a machine learning encoder model; and performing task-specific training by adding a task-specific network layer and training the task-specific network layer to map the edit-space representation to an output associated with a health condition.

By training a machine learning model to learn a representation usable to generate a candidate text based on a reference text, the representation must encode information on the differences between the candidate text and reference text. The inventors have recognised that this kind of representation is usable as a text similarity evaluation metric which captures high level information on similarity between any pair of texts. This kind of information is directly usable in the identification and monitoring of any health condition which affects speech and the ability to recall information. A key use is assessing performance in the types of memory recall task used to diagnose and monitor neurodegenerative diseases such as Alzheimer's, by analysing a person's retelling of a reference text.

Edit-space representations learned in this way are able to encode a much greater range of subtle changes in language use than the simple edit-distance-difference-based metrics of the prior art, such as the widely used BLEU and ROUGE metrics, used to evaluate machine translations. The present invention therefore facilitates diagnosis and monitoring of a wide range of health conditions more accurately and at a much earlier stage than existing measures.

During pre-training the model may be trained on widely available large unlabelled data sets, overcoming issues with limited clinical data. Using generative conditioning as the pre-training objective requires the model to learn generalised edit-space representations which encode the information required to generate a candidate based on a reference, thereby learning general purpose information. The representations may then be fine-tuned by performing subsequent task-specific training on smaller labelled data sets to provide a specific metric for any health condition for which data is available, meaning the method has vast applicability across any health condition which could induce changes in a subject's speech and, for example, the way a subject recalls a story.

Although the invention finds particular application in assessing story retelling tasks, it is noted that the method would also find application in a wide range of other tasks that elicit speech. The solution can be applied on other speech tasks (for example the description of a picture), by adopting an appropriate reference (for example a description with all details in). The solution can further be used in a task-agnostic way by comparing a candidate text to different reference texts with specific associated characteristics, for example computing whether a candidate text is more similar to reference texts of people with confirmed Alzheimer's disease or more similar to reference texts of people confirmed to be healthy.

Preferably a "representation" or "data representation" comprises a feature vector, i.e. a vector encoding important distinguishing attributes of the input data. The term embedding is used interchangeably with the term representation. Preferably a representation captures meaningful structure of the input by placing meaningfully similar inputs close together in the representation space. A representation can be learned and reused across models or at different stages of training.

An "edit space representation" is a representation which encodes information for mapping between a candidate text and a reference text. The term "paraphrase representation" is used interchangeably with edit-space representation herein.

Preferably the machine learning model comprises an attention-based model, for example a model that uses contextual information of an input sequence to form context-dependent representations, for example a model that uses the context of an element in an input sequence, where context comprises for example the position and relationship of an element in the input sequence relative to other elements in the input sequence, where an element may refer to a sub-word, word or multiple word segment, an audio segment or a sequence position. The model may preferably comprise a Transformer. The edit encoder is preferably a Transformer encoder, preferably initialised using a pre-trained language model.

In preferable examples of the invention, pre-training the edit encoder comprises generative conditioning. Generative conditioning preferably comprises training the edit-encoder to generate an edit-space representation of a particular text comparison pair that, when fed to a sequence-to-sequence encoder-decoder, allows the sequence-to-sequence encoder-decoder to map the reference text of the particular text comparison pair, input into the sequence-to-sequence encoder-decoder, to the candidate text of the particular text comparison pair. Generative conditioning preferably comprises training the edit encoder and sequence-to-sequence encoder-decoder together on a training data set comprising text comparison pairs, where during training, a text comparison pair is input into the edit encoder while just the reference text of the text comparison pair is input into the sequence-to-sequence encoder-decoder, and the edit encoder and sequence-to-sequence model and trained together with the objective of reconstructing the candidate phrase (output by the sequence-to-sequence model).

Preferably generative conditioning comprises connecting the edit encoder to a sequence-to-sequence encoder-decoder suitable for mapping an input reference text to an output candidate text, where the edit encoder is connected such that the sequence-to-sequence encoder-decoder is conditioned using the edit-space representation generated by the edit encoder; inputting a text comparison pair into the edit encoder and inputting the reference text of the text comparison pair into the sequence-to-sequence encoder-decoder; and training the edit encoder and sequence-to-sequence encoder-decoder together to map the inputs to the candidate text of the text comparison pair output by the sequence-to-sequence decoder, such that the edit encoder learns to generate an edit-space representation usable by the sequence-to-sequence encoder-decoder to generate the candidate text based on the input reference text.

In this way, the edit encoder is encouraged to learn an edit representation comprising a data representation of an input text comparison pair which encodes information which can be used to transform the reference text of the text comparison pair to the candidate text of the text generation pair. The edit representation therefore encodes information on the differences between the candidate and reference which can be used as a metric to assess similarity. The edit space representation learned in this way learns higher level information than simple text-level edits which therefore capture information closer to the higher level concepts that humans use to judge text similarity.

Put another way, generative conditioning comprises training the edit encoder and sequence-to-sequence encoder-decoder together with the objective of reconstructing the candidate tex. In particular the edit encoder is trained to learn an edit space representation which is passed to the sequence-to-sequence encoder-decoder and simultaneously the sequence-to-sequence encoder-decoder is trained to map the reference text to the candidate text using the edit-space representation. The training objective is to minimise a loss associated with the closeness of the reconstructed candidate text output by the sequence-to-sequence encoder-decoder to the input candidate text of the text-comparison pair. In other words, the models are trained to attempt to generate the candidate text as the output of the sequence-to-sequence encoder-decoder.

In some examples, the edit space representation is added to each of the representations output by the encoder of the sequence-to-sequence encoder-decoder. Put another way, the edit space representation is used by the sequence-to-sequence encoder-decoder by adding the edit space representation to each of the sequence of representations (e.g. tokens) output by the encoder of the sequence-to-sequence encoder-decoder before being passed to the decoder of the sequence-to-sequence encoder-decoder.

Preferably an information bottleneck is provided between the edit encoder and the sequence-to-sequence such that the candidate text cannot be passed in full from the edit encoder to the sequence-to-sequence encoder-decoder during training. In this way, the sequence-to-sequence encoder-decoder cannot simply receive the candidate text from the text comparison pair input into the edit encoder, but instead the edit encoder must learn higher level abstractions which it can encode more efficiently to allow the information to pass through the bottleneck. This makes it beneficial for the edit encoder to learn higher order information on the changes in speech patterns, such as patterns in reordering of words, changes in tense etc. These kind of differences in text are not encoded in simple edit-level metrics and so the edit-space representations better capture the relative importance of different types of changes in text patterns.

The information bottleneck preferably comprises a reduced dimension representation space. The information bottleneck may be provided by a feed-forward network provided between the transformer encoder and the sequence-to-sequence encoder-decoder. More particularly the information bottleneck may be arranged so it feeds information between the encoder layers and the decoder layers of the sequence-to-sequence encoder-decoder. The information bottleneck may comprise a pooling layer. The pooling layer may have a similar structure to that used in the BERT model (Devlin et al "BERT: Pre-training of Deep Bidirectional Transformers for Language Understanding" arXiv: 1810.04805v2). In particular the edit encoder may be a Transformer encoder which encodes the input text comparison pair into a sequence of tokens, where the pooling layer takes just the first token (the '[CLS]' token) in the sequence which provides a text-level representation of the sequence. In this way, the edit encoder and pooling layers are trained so as to learn a single token (i.e. a single representation) which encodes the information on the required edits. This places a restriction on the amount of information that can be encoded (i.e. contributes to the information bottleneck) thus encouraging the learning of more data efficient higher order abstractions. In some examples the edit space representation comprises the representation output by the pooling layer.

Preferably pre-training the edit encoder comprises masked language modelling (i.e. a masked language training objective), where masked language modelling comprises: providing a linear projection layer after the edit encoder; inputting a text comparison pair into the edit encoder where part of the input text-comparison pair is withheld; and training the edit encoder and the linear projection layer together to predict the withheld part of the input text-comparison pair. Using a masked language modelling objective encourages the edit encoder to perform bitext alignment between the candidate text and reference text. The machine learning model, comprising the edit encoder and linear projection layer, is trained to predict a hidden, or masked, part of the input text comparison pair. In this way, the model is trained to predict a missing part of the text based on its context, encouraging the model to learn information on the relationship between the words used. In particular, the model is encouraged to use the candidate text to predict the reference text and vice versa, strengthening the alignment bias which facilitates the generative conditioning pre-training.

Preferably the input text comparison pairs are encoded as text tokens, where each token represents a sub-word, word or multiword part of the encoded text sequence. Preferably the masked language modelling comprises masking one or more tokens and training the machine learning model to predict the masked tokens. Preferably unsupervised training is used in which the model itself randomly masks a proportion of the input tokens and then uses the remaining tokens to predict the masked tokens. This encourages the model to build a general understanding of language. In particular it encourages the edit encoder to learn edit-space representations which encoder high-level linguistic concepts rather than low-level edits, thus learning abstractions particularly relevant to clinical applications. Additionally, masked language modelling is a 'bitext alignment' (candidate-reference matching) task, which also encourages the identification of synonyms and other similarities between the texts. In these examples, a linear projection layer may be used which acts on all tokens in the sequence encoded by the edit encoder, so as to predict each masked token individually.

Preferably pre-training comprises entailment training using an entailment data set comprising text comparison pairs with an entailment label indicating whether the reference text logically entails the candidate text. Preferably the method more specifically comprises adding an entailment projection layer after the edit-encoder, the entailment projection layer trainable to predict the entailment label using the edit-space representation provided by the edit encoder; training the edit encoder and entailment projection layer to map an input text comparison pair to the entailment label. The entailment projection layer may be a classification layer, trainable to predict the entailment label based on the edit-space representation learned by the edit encoder. The entailment label may be a binary label indicating with the reference logically entails the candidate or not. Using an entailment layer encourages the edit encoder to learn an edit-space representation that encodes information on whether the candidate and reference convey the same essential meaning, rather than just being semantically similar. It therefore encourages the encoder to learn an edit-space representation that encodes higher level information on the similarity between concepts and meaning conveyed by two texts, rather than similarity based on text-level edits, such that it can recognise that a candidate and reference may be similar in meaning despite differing significant in terms of specific words used (and vice versa).

Preferably entailment training comprises adding a pooling layer between the edit encoder and the entailment projection layer (where the entailment projection layer is preferably a linear projection layer), the pooling layer configured to convert the sequence of representations (preferably tokens) output by the encoder into a single representation passed to the entailment projection layer. Preferably the edit encoder outputs a sequence of tokens and the pooling layer tokens the first (CLS) token from the sequence or takes the mean of all tokens.

Pretraining preferably comprises performing two or more of the following simultaneously: generative conditioning, masked language modelling and entailment training. Preferably pre-training may comprise a pre-training loss factor incorporating two or more individual loss factors associated with the above three pre-training methods, i.e. a generative conditioning loss factor, a masked language modelling loss factor and an entailment loss factor. Preferably the total pre-training loss factor may comprise a sum of the three individual loss-factors with a coefficient for each individual loss factor variable as tunable hyperparameters.

Preferably the Total Loss Factor May be Provided by, $$\mathcal{L}_{pre} := \mathcal{L}_{AR} + \alpha \cdot \mathcal{L}_{MLM} + \beta \cdot \mathcal{L}_{CLS}, \quad (1)$$

Where $L_{pre}$ is the full pre-training loss, $L_{AR}$ is the generative conditioning loss, $L_{MLM}$ is the masked language modelling loss, $L_{CLS}$ is the entailment loss, and $\alpha$ and $\beta$ are tunable hyperparameters.

In certain preferable examples, pre-training comprises generative conditioning and masked language modelling, performed simultaneously. The entailment loss may optionally also be included.

Preferably pre-training comprises performing unsupervised training on a pre-training data set comprising text comparison pairs, in particular unlabelled text comparison pairs. The unlabelled text comparison pairs may comprise paraphrase pairs, where paraphrase pairs comprise a reference text and a candidate text comprising a paraphrased version of the reference text.

Preferably performing task specific training comprises: training the task-specific network layer using a task-specific data set comprising labelled text comparison pairs, where the labelled text comparison pairs are input into the edit encoder and the task-specific layer is trained to predict the label. Pre-training the model using unsupervised learning allows the use of widely available unlabelled data sets, after which the edit-encoder is already able to generate edit-space representations which encode significant general purpose information on the similarity between two text sequences and therefore are usable as a metric to assess high level similarity for the monitoring or diagnosis of a health condition. Task-specific training allows for one or both of (1) the edit encoder to be further trained to optimise the edit-space representations that are learned for a particular task or health condition; and (2) the pre-trained edit-space representation to be used for a health condition monitoring/diagnosis/analysis task. Given the edit space representations already encode a large amount of relevant information, task-specific training can use relatively small labelled data sets. The task-specific layer may be trained independently of the edit encoder or simultaneously with the edit encoder.

Preferably performing task specific training comprises freezing one or more layers of the edit-encoder after pre-training inputting a labelled text-comparison pair and training only the task-specific network layer to map the edit-space representation generated by the frozen edit-encoder; or training the edit-encoder and the task-specific layer together such that the edit encoder learns further modified edit-space representations optimised for a specific task.

"Freezing" the edit encoder means that the weights of the model are not further adjusted during task-specific training. Put another way, the method comprises fixing the weights of the edit-encoder and training the task-specific layer alone. The entirety of the edit encoder may be frozen or one or more layers may be frozen.

The task-specific data set preferably comprises labelled text comparison pairs, each comprising a label associated with at least one of: a human-derived measure of the similarity of the text comparison pair; a health condition of the speaker of the candidate text.

By inputting text comparison pairs and training a task specific layer to map the edit-space representation to a human-derived measure of the similarity of the text comparison pair, the model may be trained to output a measure of the similarity of any input text comparison pair. This method has exceeded previous state of the art performance in predicting an average human assessment of similarity, using smaller data sets than that used in the prior art. The model trained in this way may be used, for example, to assess the similarity between a reference text and a recalled version of the text spoken by a subject in a memory recall task, which gives a much more accurate, and human, assessment of the true similarity between the texts. The method is therefore usable to identify health conditions that affect memory and/or speech and has the potential to identify neurodegenerative conditions such as Alzheimer's disease years earlier than present tests.

By inputting text comparison pairs and training a task specific layer to map the edit-space representation to a label associated with a health condition associated with a speaker of the candidate text, the model may be trained to a health condition prediction of any input text comparison pair. For example, the task-specific data set may comprise text comparison pairs comprising a reference text, a candidate text associated with speech from a subject with or without a health condition and a label indicating whether the subject has or does not have a health condition, where the health condition may be for example a neurodegenerative condition. Edit-space representations learned in this way encode information predictive for the trained health condition. The method may therefore be used to identify, monitor or otherwise evaluate a health condition.

Preferably the task-specific data set comprises text comparison pairs, each comprising a label associated with a health condition of the speaker of the candidate text, where the health condition comprises one or more of: a neurodegenerative disease, neurobehavioral condition, head injury, stroke, or a psychiatric condition.

Preferably the task-specific layer comprises one or more of: a classification layer for classifying an edit-space representation into one or more categories; a regression layer for providing a value, score or measure associated with a health condition; a clustering layer for identifying patterns in edit-space representations.

Preferably the method comprises, prior to performing pre-training, initialising the edit encoder and/or the sequence-to-sequence encoder-decoder using a pre-trained language model. The method may comprise initialising the weights of the edit encoder and/or the sequence-to-sequence encoder-decoder. Using a pre-trained language model means that the model has been initialised with basic language understanding to improve the efficiency of the pre-training process. Initialising the model may comprise performing initialisation training, where initialisation training comprises unsupervised training on unlabelled text data. For example the edit encoder may be a Transformer encoder initialised from a pretrained Longformer encoder and the sequence-to-sequence encoder-decoder a Transformer encoder-decoder initialised from a pre-trained BART model.

A text comparison pair preferably comprises a data sequence comprising a candidate text and a concatenated reference text. In particular the candidate text and reference text may be combined in a single input sequence. Preferably the text comparison pair may comprise a plurality of concatenated candidate texts followed by a plurality of concatenated reference texts.

Each reference text and each candidate text preferably comprises a sequence of text tokens, each text token encoding a sub-word, word or multiple word sequence. Therefore a text comparison pair may comprise a sequence of text tokens. Tokenising the input reduces the processing requirements for the model and facilitates training. A token preferably comprises a (preferably contextual) representation of a sub-word, word, or multiple word segment of text In some examples the method comprises task-adaptive training, where task-adaptive training comprises pre-training the edit encoder using clinical data, for example labelled text comparison pair data. In particular task-adaptive training may comprise performing generative conditioning training using clinical data, where clinical data may comprise text comparison pairs where the candidate and/or reference text corresponds to speech from a subject with a health condition or healthy controls. Training may preferably comprise pre-training with unlabelled data and then performing task-adaptive training by continuing to pre-train with clinical data. Preferably the method comprises freezing the edit encoder (or one or more layers of the edit encoder) after task-adaptive training and preferably then using the frozen edit encoder to generate edit-space representations to be used in diagnosing and/or monitoring a health condition.

In another aspect of the invention there is provided a computer implemented method of training a machine learning model to evaluate the similarity of a candidate text to a reference text for determining or monitoring a health condition, where the machine learning model takes as input a text comparison pair, where a text comparison pair comprises a reference text and a candidate text, each comprising data encoding a text sequence, the method comprising: pre-training an edit encoder to learn an edit-space representation of a text comparison pair, where the edit-space representation encodes information for mapping the reference text to the candidate text, the edit encoder comprising a machine learning encoder model.

In particular, although in the first aspect the method of training comprises a task-specific training step, in other examples of the invention the method may not include a task specific training step. This is because, even after pre-training alone, the edit-space representations are usable to monitor or diagnose a health condition. In particular, the pre-training methods described above result in an encoder capable of encoding input text comparison pairs into edit-space representations which contain information on the differences between the candidate and reference which can be indicative of the presence or changes in a health condition. For example, as defined below, a method of using the pre-trained encoder may comprise inputting text comparison pairs comprising candidate text associated with a test subject and analysing the representations, for example using clustering, to determine patterns indicative of health conditions. Furthermore the pre-trained model may be used to generate edit-space representations for a test subject and compare these to edit-space representations from one or more healthy subjects and/or edit space representations from one or more subjects with a known health condition.

The additional preferable aspects of the pre-training method described above apply equally to methods without a task-specific training step. In particular, pre-training may comprises generative conditioning as defined herein, preferably with an information bottleneck.

In another aspect of the invention there is provided a computer implemented method of using a machine learning model to evaluate the similarity of a candidate text to a reference text to determine or monitor a health condition, where the machine learning model takes as input a text comparison pair, where a text comparison pair comprises a reference text and a candidate text, each comprising data encoding a text sequence, the method comprising: inputting the text comparison pair into a trained machine learning model, the machine learning model comprising an edit encoder trained to generate an edit-space representation that encodes information for mapping the candidate text to the reference text; using the edit-space representation to evaluate the similarity of the candidate text to the reference text to determine or monitor a health condition.

Since the edit-space representations output by the pre-trained model (i.e. prior to task-specific training) encode information for assessing the similarity between a candidate text and a reference text they may be used to evaluate the similarity of two texts to determine or monitor a health condition. A notable example includes use for memory recall tasks where the edit-space representations for a reference text and a recalled version of the reference text (the candidate text) may be used as a metric (or to map to a metric) to analyse the similarity to diagnose or monitor a neurodegenerative disease such as Alzheimer's disease. However the suitability of the edit-space representations for encoding high level patterns in changes between texts means they are widely applicable for a broad range of clinical applications.

Using the edit-space representation to evaluate the similarity of the candidate text to the reference text to determine or monitor a health condition may comprise analysing the edit-space representations directly (for example performing clustering on the representations, or comparing representations to identify differences or similarities to health subjects or subjects with a health condition) or using another model or layer to provide a health condition prediction using the edit space representations.

The candidate text may encode text data corresponding to a transcript of speech from a subject, the method comprising using the edit-space representation to determine or monitor a health condition of the subject. In this way, the method may be applied to a broad range of tasks for assessing the speech of a subject to diagnose or monitor a health condition. Such tasks included memory recall tasks where the candidate text comprises a transcript of a user's spoken recollection of the reference text. However they also include other spoken tasks such as asking a subject to describe a picture or object, where the candidate text comprises a transcript of a subject's spoken description and the reference text comprises a reference description including expected features of the picture or object.

Using the edit-space representation to evaluate the similarity of the candidate text to the reference text to determine or monitor a health condition preferably comprises: comparing an edit-space representation of a text comparison pair from a test subject with an edit-space representation of a text comparison pair from a healthy subject and/or a subject with a health condition. In these examples, models need not have been trained on clinical data. The model is usable after pre-training alone, although may be further optimised with task-specific or task-adaptive training, as described above. Since the edit-space representation encodes clinically relevant information on the closeness of the candidate to the reference text, it is usable for clinical tasks, even after pre-training alone.

The method may comprise comparing the edit space representation of a text-comparison pair from a test subject to an average edit space representation averaged over a plurality of health subjects and/or subjects with a health condition.

Using the edit-space representation may comprise performing cluster analysis on the edit-space representation to identify trends indicative of a health condition.

In other examples of the method, the machine learning model comprises a linear projection layer for mapping an edit-space representation generated by the edit-encoder to an output associated with a health condition prediction and wherein using the edit-space representation to evaluate the similarity of the candidate text to the reference text to determine or monitor a health condition comprises: inputting a text comparison pair from a test subject into the machine learning model to provide a health condition prediction.

In contrast to the above examples of the method comprising analysing the edit-space representations themselves to identify patterns indicative of health conditions, in these examples the machine learning model comprises an additional layer or model for making a health condition prediction based on the edit-space representation generated for an input text comparison pair. The linear projection layer may comprise a task-specific network layer as defined above. The linear projection layer may be a network layer trained to map an edit space representation to one or more of: a predicted human-derived measure of the similarity between the candidate text and reference text; an output associated with a health condition for example a health condition diagnosis, probability or predicted stage of progression. The linear projection layer may comprise a classification layer or a regression layer.

The machine learning model is preferably trained using one or more steps defined above under the first aspect or in the appended claims. Machine learning models trained in this way are identifiable by testing carried out to the trained model. In particular the machine learning model may be trained solely using the pre-training steps and not the task-specific steps. In particular the machine learning model may comprise an edit-encoder trained by generative conditioning, where generative conditioning comprises: connecting the edit encoder to a sequence-to-sequence encoder-decoder suitable for mapping an input reference text to an output candidate text, where the edit encoder is connected such that the sequence-to-sequence encoder-decoder is conditioned using the edit-space representation generated by the edit encoder; inputting a text comparison pair into the edit encoder and inputting the reference text of the text comparison pair into the sequence-to-sequence encoder-decoder; and training the edit encoder and sequence-to-sequence encoder-decoder together to map the inputs to the candidate text of the text comparison pair output by the sequence-to-sequence decoder, such that the edit encoder learns to generate an edit-space representation usable by the sequence-to-sequence encoder-decoder to generate the candidate text based on the input reference text.

Preferably the text comparison pair input into the trained model comprises one or more of the features described above under methods of training the model. A text comparison pair preferably comprises a data sequence comprising a candidate text and a concatenated reference text. In particular the candidate text and reference text may be combined in a single input sequence.

Each reference text and each candidate text preferably comprises a sequence of text tokens, each text token encoding a sub-word, word or multiple word sequence. Therefore a text comparison pair may comprise a sequence of text tokens. Tokenising the input reduces the processing requirements for the model and facilitates training. A token preferably comprises a (preferably contextual) representation of a sub-word, word, or multiple word segment of text.

As described above, preferably the trained edit encoder is trained with an information bottleneck provided between the edit encoder and the sequence-to-sequence encoder-decoder such that the candidate text cannot be passed in full from the edit encoder to the sequence-to-sequence encoder-decoder during training.

Although in the above aspects the method is used for clinical applications, it may equally be used in other applications in which an improved assessment of the similarity between two text sequences is desirable.

In particular, in another aspect of the invention there is provided a computer implemented method of training a machine learning model to evaluate the similarity of a candidate text to a reference text, where the model takes as input a text comparison pair, where a text comparison pair comprises a reference text and a candidate text, each comprising a text data sequence, the method comprising: pre-training an edit encoder to learn an edit-space representation of a text comparison pair, where the edit-space representation encodes information for mapping the reference text to the candidate text, the edit encoder comprising a machine learning encoder model. In this way the edit encoder is trained to generate an edit-space representation for any input text comparison pair, where the edit-space generation is usable as a metric to assess the similarity of the reference text and candidate text.

The method may further comprise task-specific training where task-specific training preferably comprises adding a task-specific network layer and training the task-specific network layer to map an edit-space representation generated by the pre-trained edit encoder to an output associated with a text similarity metric. In particular, the method may comprise performing task-specific training with a task-specific data set, where the task-specific data set comprises labelled text comparison pairs, each comprising a label associated with a human-derived measure of the similarity of the text comparison pair, for example an average human score of the similarity of the reference and candidate texts.

Aspects of the training method defined above and in the appended claims apply equally to these aspects where task-specific training associated with a health condition is replaced with task-specific training associated with a measure of text similarity.

In a related aspect there is provided a computer implemented method of using a machine learning model to evaluate the similarity of a candidate text to a reference text, where the model takes as input a text comparison pair, where a text comparison pair comprises a reference text and a candidate text, each comprising a text data sequence, the method comprising: inputting the text comparison pair into a trained machine learning model, the model comprising an edit encoder trained to generate an edit-space representation that encodes information for mapping the candidate text to the reference text; and using the edit-space representation to evaluate the similarity of the candidate text to the reference text. In this way, two texts may be input into the trained model as a text comparison pair such that the model outputs a measure of their similarity in the form of the edit-space representation. The model may comprise an additional task-specific layer, such as a classifier or regression model, for mapping the edit-space representation to a text similarity evaluation score.

In another aspect there is provided a system for evaluating the similarity of a candidate text to a reference text to determine or monitor a health condition, the system comprising a processor configured to: receive a text comparison pair, where a text comparison pair comprises a reference text and a candidate text, each comprising data encoding a text sequence; providing a health condition prediction by inputting the text comparison pair into a trained machine learning model, the machine learning model comprising an edit encoder trained to generate an edit-space representation that encodes information for mapping the candidate text to the reference text, and a linear projection layer trained to map an edit-space representation generated by the edit-encoder to an output associated with a health condition prediction. In particular the system may be a computer device. The system may be incorporated into a medical device for providing a health condition prediction. The system may comprise a distributed computing system. The system may be configured to send the text comparison pair to a remote processor for processing using the trained model. In this way, the input may be received locally and sent to a remote server for processing, i.e. the machine learning model may be hosted on a remote server.

The system may comprise a smart phone, a computer, tablet device or a smart speaker, preferably configured to send the input comparison pair to a remote processor for processing using a machine learning model, with the health condition prediction returned.

The system preferably comprises an audio input for receiving speech from a subject, where the speech data may comprise raw audio data. The system preferably comprises an automatic speech recognition module for processing the speech to extract data encoding a transcript of the speech. The system may be configured to form a candidate text using the data encoding a transcript of the speech. That is, the candidate text may comprise data encoding a text sequence where the text sequence is the transcript of the input speech. The system may comprise a display for displaying a reference text to a user. The system may comprise an audio output for playing audio comprising speech corresponding to the reference text. The system may be configured to prepare an input text comparison pair from the candidate text and the reference text and send this to the trained machine learning model for processing. The system preferably comprises a communications link for sending the prepared text comparison pair to the trained machine learning model.

In another aspect there is provided a system comprising one or more processors configured to perform one or more of the computer implemented methods described above or in the appended claims.

BRIEF DESCRIPTION OF THE DRAWINGS

Embodiments of the present invention are described below, by way of example only, with reference to the accompanying drawings, in which.

DETAILED DESCRIPTION

Figure 1:
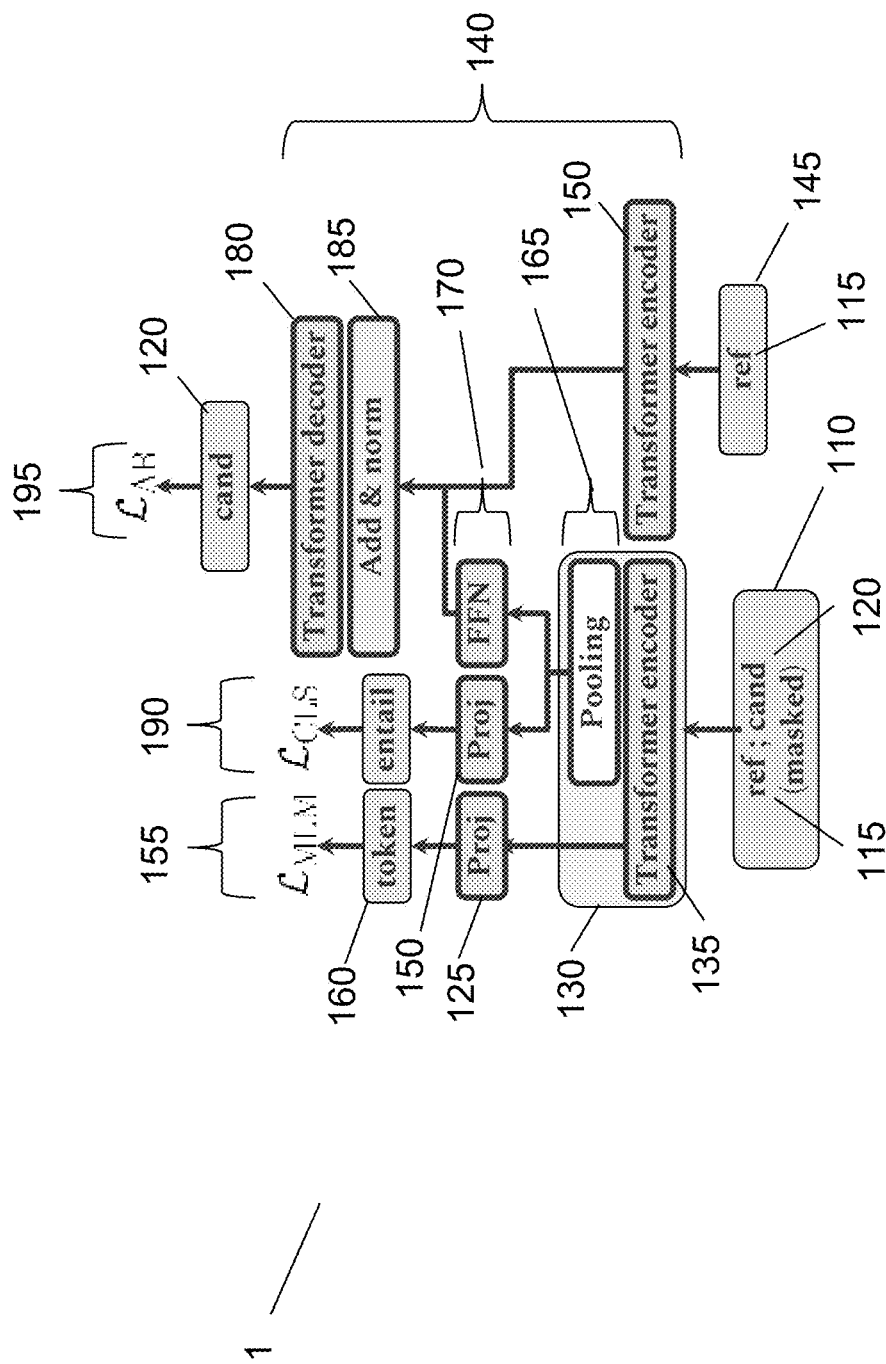
FIG. 1 illustrates in schematic form a pre-training model according to the present invention.

The present disclosure describe methods for training a machine learning model to learn representations for evaluating the similarity between a reference text and candidate text, which captures a greater range of high level changes in the use of language and therefore is usable to diagnose and monitor a wide range of health conditions that affect memory, language and/or speech.

Theoretical Basis for the Method

A set of inductive biases are used to establish a function: $f(x,\hat{x}) \to y$, between a reference text x and a candidate text $\hat{x}$, where $y \in \mathbb{R}^N$ is a single or multi-dimensional edit-space representation, which could be a scalar score. Below, the term "paraphrase representation" is used interchangeably with "edit-space representation" to mean a data representation which encodes a mapping between a reference text and a candidate text.

Furthermore, the machine learning method of the present disclosure utilises an approach that decomposes edit-space representation learning into three possible overlapping factors:

1. Edit-space representation learning: Building a representation of high-level syntactic and semantic differences between x and $\hat{x}$, contrasted with the low-level pseudo-syntactic/-semantic operations considered by edit-distance-based and n-gram based metrics.
2. Candidate acceptability judgement: Evaluating the grammaticality, coherence and naturalness of z in isolation. Perplexity [Fred Jelinek et al, "Perplexity—a measure of the difficulty of speech recognition tasks" *The Journal of the Acoustical Society of America*, 62(S1):S63-S63, 1977] with respect to a given language model is one proxy for this.
3. Semantic equivalence: Assessing whether x and $\hat{x}$ convey the same essential meaning precisely, as opposed to merely being semantically similar. This is related to entailment classification tasks and, more broadly, the interaction between language and formal logic.

Exploiting this factorization, the following inductive biases have been identified as being beneficial to a edit-space representation learning model:

Using pretrained language models: All three factors benefit from a general understanding of the semantic and syntactic structures of language, making transfer learning from powerful pretrained language models such as BERT [Jacob Devlin et al "Bert: Pre-training of deep bidirectional transformers for language understanding". *arXiv preprint arXiv:*1810.04805, 2018] appealing.

Non-local attention as bitext alignment: Factors (1) and (3) require performing context aware 'matching' between x and $\hat{x}$. This is similar to the statistical method of bitext alignment [Jörg Tiedemann. *Bitext alignment. Synthesis Lectures on Human Language Technologies*, 4(2):1-165, 2011]. Attention mechanisms within a Transformer [Ashish Vaswani et al "Attention is all you need" *arXiv preprint arXiv:*1706.03762, 2017] are an obvious candidate for learnable context-aware matching, which has precedent in paraphrasing tasks and the next-sentence-prediction objective of the original BERT pretraining [Tianyi Zhang et al, "Bertscore: Evaluating text generation with bert". *arXiv preprint arXiv:*1904.09675, 2019] [Thibault Sellam et al, "Bleurt: Learning robust metrics for text generation" *arXiv preprint arXiv:*2004.04696, 2020]. We note that x and x̂ side-by-side violates attention locality, meaning local attention mechanisms, such as those used in T5 [Raffel et al "Exploring the Limits of Transfer Learning with a Unified Text-to-Text Transformer". arXiv:1910.10683v3] may be suboptimal for longer text-pairs.

Bottlenecked conditional generation objective: A further key insight is that a strong factor (1) representation $z \in R^M$ where $h: h(x,\hat{x}) \to z$ is one that can condition the sampling of $\hat{x}$ from x using a generative model $g: g(x|z) \to \hat{x}$. One trivial solution to this is $h: h(x,\hat{x}) = \hat{x}$. To avoid this case, we preferably introduce an information bottleneck on z such that it is advantageous for the model to learn to represent high-level abstractions, which are cheaper than copying $\hat{x}$ through the bottleneck if they are sufficiently abstract compared with $\hat{x}$, the bottleneck is sufficiently tight, and the decoder can jointly learn the same abstractions. It has also been determined that it is advantageous to use a pretrained sequence-to-sequence language model, which can already reason in linguistic concepts.

Masked language modelling objective: Factor (2) can be addressed by an MLM objective, which alone is sufficient for a neural network to learn a language model [Jacob Devlin et al, "Bert: Pre-training of deep bidirectional transformers for language understanding" arXiv preprint arXiv:1810.04805, 2018]. Performing masked language modelling on a reference-candidate pair also encourages the network to use x to help unmask $\hat{x}$ and vice versa, strengthening the alignment bias useful for factors (1) and (2).

Entailment classification objective: Factor (3) is similar to the classification of whether x logically entails $\hat{x}$. This can be achieved by training with sentence-pair datasets with entailment labels to construct an entailment loss.

These implementation features each contribute to ensuring a selected edit-encoder learns information dense edit-space representations for mapping a reference text to a candidate text. They may be employed individually or in combination. Of these it has been determined that a generative objective—training an encoder to learn an edit-space representation that is usable to generate the candidate based on the reference—is a key feature in pre-training the edit encoder to generate edit-space representations usable in a wide range of clinical applications.

As such, factorization of edit-space representation learning leads to three complementary training objectives usable to train an edit encoder to learn edit space representations which encode the similarity of two pieces of text:

(1) Cross-entropy masked language modelling loss, $L_{MLM}$;
(2) Binary cross-entropy entailment classification loss, $L_{CLS}$, and
(3) Cross-entropy autoregressive causal language modelling loss, $L_{AR}$.

An additional sequence-to-sequence transformer model is used during pre-training to provide a learning signal for the edit encoder. If all three training objectives are applied, the full pre-training loss is given by equation (1) below:

$$\mathcal{L}_{pre} := \mathcal{L}_{AR} + \alpha \cdot \mathcal{L}_{MLM} + \beta \cdot \mathcal{L}_{CLS}, \quad (1)$$

where $\alpha$ and $\beta$ are tunable hyperparameters.

However in other examples only one or two of these training objectives are applied, for example the generative conditioning loss (Cross-entropy autoregressive causal language modelling loss, $L_{AR}$) preferably in combination with another, such as the Cross-entropy masked language modelling loss, $L_{MLM}$.

As such the above overlapping factorisation can be exploited to develop the present edit-space representation learning model in which information required to generate a paraphrase, or candidate phrase, from a reference text is encoded from corresponding pairs of phrases (the term phrase is used generally to refer to a text sequence of any length), as will be explained further with reference to FIG. 1.

Specific Example of Model Architecture and Training Method

FIG. 1 schematically illustrates an overview of an example model architecture 1 used in the pre-training steps of the computer-implemented method for training a machine learning model network according to the present invention.

In this example the input to the model is illustrated with the example of comparing a reference text or phrase to a paraphrased version of the reference text or phrase—the latter referred to as a "candidate text" or "candidate phrase". This is to illustrate the method in the context of a memory recall task or similar where a subject must recall a reference text and therefore their response comprises a paraphrase of varying similarity to the reference phrase. It should be noted that the method can be applied to any two portions of text, of any length, where they may not be strict paraphrases, to evaluate the similarity of the text. Therefore the terms "candidate phrase" and "reference phrase" are used equivalently and interchangeably with "candidate text" and "reference text". Similarly, in the context of this example the input reference phrase and candidate phrase are referred to as a "paraphrase pair" but this is completely interchangeable with the more general "text-comparison pair" or "text pair" used elsewhere herein.

The network 1 is trained using a pre-training data set comprising a plurality of paraphrase pairs 110, which are input into the edit encoder 130. Each text paraphrase pair 110 includes a reference text 115 and a candidate text 120 (equivalently referred to as a reference phrase and a candidate phrase). The reference text 115 and the candidate text 120 are data sequences encoding a text sequence. They may comprise text data but preferably they are formed by a sequence of text tokens (e.g. quantised text representations), to facilitate processing of the text data by the model. Input text may be tokenised by an suitable known method. It should be understood that the division of a same sequence of words can be performed in different ways, for example by sub-words, individual words or a small collection of words. In this specific example the candidate phrase 120 text is a paraphrase of at least a portion of the reference phrase 115 text.

In this example the input paraphrase pair 110 may be up to 1,024 tokens in length, although this is only limited by the increasing processing requirement. In this way, an input paraphrase pair 110 comprises a sequence of text tokens which first lists all the reference phrase tokens followed by all the candidate phrase tokens to provide a dataset with a text sequence of "<s> ref</s></s> cand </s>", where <s> and </s> are the special beginning-/end-of-sequence tokens respectively, and "</s></s>" is used in the middle to separate the reference phrase from the candidate phrases. The paraphrase pair (equivalently referred to as the text comparison pair) 110 is sent to the edit encoder 130 in the machine learning model with a certain proportion of the tokens of the paraphrase pair 110 randomly masked. Masking of the paraphrase pair 110 involves hiding, or obscuring, at least a portion of the text sequence of the candidate phrase 120 and/or the reference phrase 115 with a predetermined probability, e.g. 30% probability. Edit encoder 130 comprises a Transformer encoder-decoder 135 and is used to determine a cross-entropy masked language modelling loss $L_{MLM}$.

The edit encoder 130 is connected to a sequence-to-sequence model 140 comprising an encoder-decoder 150, 180 for pre-training of the edit encoder 130. The sequence-to-sequence model 140 is trained to map the reference phrase 115, input into its encoder 150, to the candidate phrase 120 output by its decoder. As will be described in more detail below, the edit encoder is connected so as to provide the edit-space representation to the sequence-to-sequence model 140 so that the sequence-to-sequence model can attempt to reconstruct the candidate phrase 120 based on the reference phrase 115 and the edit-space representation. The edit encoder 130 and the sequence-to-sequence model 140 are trained together according to a cross-entropy autoregressive causal language modelling loss, $L_{AR}$ 195, associated with the model's relative success in reconstructing the candidate phrase 120.

The weights in the encoders (edit encoder 130, Transformer encoder 150, and/or decoder 180) are preferably initialized using a pre-trained language model, transferred from known models such as RoBERTA or Longformer normal pre-trained on written documents. Thus, in the present network architecture, edit encoder 130 is initialised from a pre-trained Longformer encoder, and the other transformer encoder 150 (and decoder 180) from a pre-trained BART model, which is a text-to-text model. In this way learning from powerful pre-trained language models such as BERT can be transferred into present method.

To implement the first pre-training objective, the model is trained with a cross-entropy masked language modelling loss $L_{MLM}$ 155, related to the 'candidate acceptability judgement' factor (factor 2 above), where edit encoder 130 performs a linear projection, in particular a masked language modelling step, on the reference phrase 115 and candidate phrase 120 pair(s) by using reference phrase 115 to help unmask candidate phrase 120 and vice versa, thereby strengthening an alignment bias useful for factors (1) and (2).

To put it in another way, the edit encoder 130 is trained, together with a linear projection layer 125 to predict the masked portion of the paraphrase pair 110, using unsupervised learning, with a masked language modelling loss $L_{MLM}$. This $L_{MLM}$ determination process trains edit encoder 130 to perform 'bitext alignment' by using candidate phrase 120 to help unmask the reference phrase 115 and vice versa, as well as guessing words from context.

To implement the third pre-training objective, cross-entropy autoregressive causal language modelling loss $L_{AR}$, an information bottleneck is created between the edit encoder 130 and the sequence-to-sequence model 140, in this case using a pooling layer 165 and a feedforward network (FFN) 170. It is possible for $L_{AR}$ to be solved trivially (except for the masking) by just copying candidate phrase(s) 120 from the paraphrase pair 110 provided to the edit encoder 130. However, the strict pooling+FFN bottleneck restricts the amount of information that can be passed from the edit encoder 130 to the sequence-to-sequence model 140, ensuring that the candidate phrase(s) 120 cannot be copied over/passed through to the sequence-to-sequence model due to insufficient capacity at the bottleneck.

The pooling+FFN bottleneck is created as follows. A pooling layer 165 is provided at the output of the edit encoder 130, where the action of the pooling layer 165 is to take the special token [CLS] at the beginning of the token sequence output by the edit encoder, where the [CLS] token is a special token which provides a text-level representation for the entire sequence and is generally used for classification. The pooling process is then combined with a feedforward network (FFN) at step 170 to further restrict the data that can be passed through to create the pooling+FFN bottleneck. This forces the edit encoder to learn edit-space representations which encode the edit information in the form of high-level concepts (i.e. to restructure in this way, adopt this style, etc. . . . ) in order to pass through the bottleneck.

The 'Add & norm' function 185 acts as a communication channel in which the output of edit encoder 150 (via the bottleneck) and the output of the other transformer encoder 150 are added together and normalised, such that edit encoder 130 provides information to transformer decoder 180 on how reference phrase(s) 115 needs to be paraphrased in order to match candidate phrase(s) 120. In this way cross-entropy autoregressive causal language modelling loss ($L_{AR}$ loss) is determined as the candidate phrase 120 text is produced.

The machine learning model pre-training network 1 is trained end-to-end. During training, the determined $L_{AR}$ loss is multiplied by a predetermined constant (i.e. a tunable hyperparameter) and added to the determined $L_{MLM}$ loss resulting in the loss function optimised by the model. The present network can thereby be trained with two training objectives simultaneously to minimize joint loss.

The pre-training model architecture 1 may include additional components to allow for the edit encoder to be pre-trained according to the second training objective indicated above, binary cross-entropy entailment classification loss, $L_{CLS}$. For the entailment training objective, the model 1 must be trained using a labelled data set comprising paraphrase pairs {ref, cand, (entail)}, where ref is the original piece of text, cand is the paraphrased piece of text, and (entail) is an optional binary target that is true if ref entails cand (according to logical entailment).

For pre-training with the entailment objective, labelled paraphrase pairs 110 are input into the edit encoder 130 and the edit encoder 130 is trained to predict the entailment label using a linear projection layer map the edit-space representation to the label, with the aim of minimising $L_{CLS}$. The entailment pre-training objective may be combined with the masked language modelling and generative conditioning training (cross-entropy autoregressive causal language modelling loss LAR). Entailment loss may not be used in certain situations. In particular, when this value is unknown or for convenience when preparing the paraphrase dataset An example of the pre-training method of the model architecture 1 shown in FIG. 1 is therefore as follows:
1. Create a training data set of paraphrase pairs 110 comprising reference/candidate text pairs up to 1,024 tokens in length. Each paraphrase pair comprises a token sequence include the reference phrase and then the candidate phrase, first the reference phrase(s) 115 then the candidate phrase(s) 120. This is denoted as "ref; cand", as in FIG. 1.
2. Initialize the weights using a pretrained language model (i.e. not randomly but utilising an existing language model to initialise the network with some understanding of language). This information is easily transferred from e.g. RoBERTA or Longformer normal pretrained on written documents. Since the network architecture is novel, initialize edit encoder 130 from a pretrained Longformer encoder, and initialize the other transformer encoder 150+decoder 180 from a pretrained BART model, which is a text-to-text model. Transformer encoder 150 and decoder 180 is used to produce text for the $L_{AR}$ loss.

3. Pass the paraphrase pairs 110 into the network in two ways: "ref cand" is randomly masked with 30% probability and passed to edit encoder 130. ref (not masked) is additionally passed to transformer encoder 150.
4. Where entailment loss is not being used, there is a twofold objective: (i) unmask the masked "ref; cand" ($L_{MLM}$ in FIG. 1), and reconstruct the cand ($L_{AR}$ in FIG. 1). Where entailment loss is used as an additional training signal, as shown in FIG. 1, there is a threefold objective as described above.

$L_{MLM}$ encourages edit encoder 130 to perform 'bitext alignment' and use the candidate phrases 120 to help unmask the reference phrases 115 and vice versa, as well as guessing words from context.

It would be possible for $L_{AR}$ to be solved (i.e. the target candidate phrase to be generated by the sequence-sequence encoder) trivially by just copying the candidate phrases 120 from the database 110 input. Therefore, a strict bottleneck is created (provided by Pooling+FFN in FIG. 1), such that candidate phrases 120 cannot be copied from the edit encoder input to the sequence-to-sequence model because there is not enough capacity.

5. Edit encoder 130 transmits information to the rest of the network using the 'Add & norm' function as a communication channel.
6. The model network (including the edit encoder and sequence-to-sequence model) is trained end-to-end. Then the $L_{AR}$ loss is multiplied by a predetermined constant and added to the $L_{MLM}$ loss.

Figure 2:
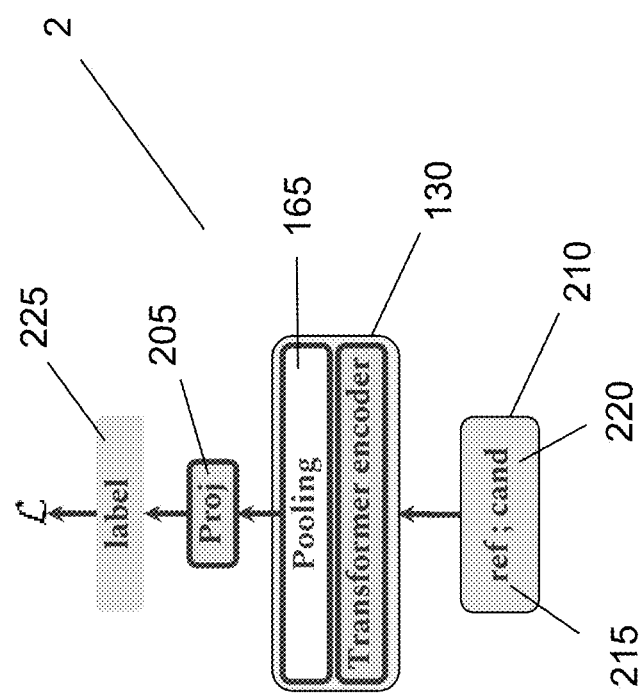
FIG. 2 illustrates in schematic form a fine-tuning model according to another embodiment of the present invention.

FIG. 2 schematically illustrates an architecture 2 for performing task-specific training for further optimising the machine learning model network according to the present invention. At the fine-tuning stage, the sequence-to-sequence training model of FIG. 1 is set aside and the model 2 is fine-tuned using a linear projection layer 205 on top of the edit encoder 130. The linear projection layer 205 is an example of a task-specific network layer and is trainable to map an edit-space representation generated by the edit encoder 130 to a particular output or label Task-specific training uses a task-specific data set comprising labelled text pair 210 including a reference phrase 215, a candidate phrase 220 and a label 225. For example, the dataset may comprise a reference text and a recalled version of the text by a subject, with a label indicating whether the subject suffers from Alzheimer's disease.

A labelled paraphrase pair 210 is input into the pre-trained edit encoder 130 such that the edit encoder 130 generates an edit-space representation encoding the differences between the reference and candidate texts 215, 220. As before the model may comprise a pooling layer 165 (preferably the same pooling layer 165 used during pre-training) which takes just the first token comprising a representation which encodes the entire output sequence, where, in this example, this first token is the edit-space representation. In other examples, the edit space representation may be considered the sequence of representations output by the edit encoder 130. The linear projection (or task-specific) layer 205 is trained to map the edit-space representation to the label (e.g. Alzheimer's disease prediction). In this way the trained model can provide an Alzheimer's disease prediction for any input paraphrase pair 210.

There are a number of options for how the task-specific training may be implemented. In some examples, the edit encoder 130 may be frozen after pre-training (i.e. all or some of the weights in one or more or all layers fixed after pre-training) and it is just the task-specific layer 205 which is trained during task-specific training (the task-specific layer may be a simple classification or regression layer). This is because the pre-training method is such that the edit-space representations of the pre-trained model already encode clinically relevant information usable to make a health condition prediction and therefore further fine-tuning of the representations is not necessary.

In another example the edit encoder may continue to be trained during task-specific training. In particular, the edit encoder and the task-specific layer may be trained together to map an input paraphrase pair 210 to the corresponding label 225. This further optimises the edit-space representations to capture additional information for the specific task.

A specific clinical example of the task specific training will now be described. Participants in a clinical trial have been told a story of around 200 words, which they then need to repeat back. Participants will either have early stage Alzheimer's disease or be healthy controls. This data set therefore comprises labelled text pairs 210 {ref, cand, ad}, where ref is the text data of the story they were told, cand is the text data of their transcribed response, and ad is whether the speaker has early stage Alzheimer's disease. The following steps are taken:

1. Using the trained/pre-trained edit encoder 130 (trained using the method of FIG. 1), add a single linear projection (a simple learnable layer) on top of the original pooling (if a pooling layer is used).
2. A typical setup is thus provided by using the pre-trained edit encoder (e.g. a Transformer encoder), pooling by taking the first classification token, with a linear projection on top. The pre-training method provides a greatly improved initialization for the weights in the edit encoder 130 is provided through the training/pre-training process. This means that the edit encoder 130 is primed for understanding paraphrases in a high-level, conceptual way.
3. Text pair {ref, cand} is fed into pre-trained edit encoder 130 as input and the parameter {ad} is used as a target with binary cross-entropy loss and the whole network is fine-tuned end-to-end. Unlike in the pre-training method, the "ref cand" text pair and database is not masked in the fine-tuning stage.
4. Once task-specific training has been carried out, at inference time (i.e. to make a health condition prediction), a paraphrase pair, "ref cand", is passed in for a new speaker and a prediction for {ad} is produced.

The trained model 2 may therefore be incorporated in a medical device to provide a Alzheimer's diagnosis prediction on the basis of an input paraphrase pair.

Figure 3:
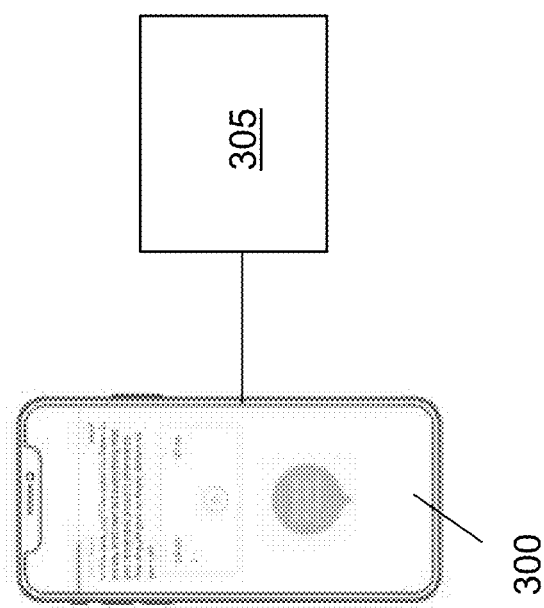
FIG. 3 shows a computing device in which the present invention can be implemented.

FIG. 3 shows a computing device 300 in which the described machine learning methods can be implemented. The computing device 300 is a standard smartphone, but it should be appreciated that the described methods can be implemented in other computing devices such as a computer or tablet device, a smart speaker, in the cloud, and via a standard phone. Computing device 300 is linked to a machine learning model network 305 such that story recall tasks or other language diagnostic processes can be performed remotely in a fully self-supervised manner.

While the above describes specific examples of the clinical rationale of using general text evaluation methods to compare retellings to a target story, the broader application is that these methods could be used for comparing any sets of speech. For example the speech of someone with an unknown diagnosis could be compared to speech samples from a group with a known Alzheimer's diagnosis and a group that's known to be healthy, to determine if it's more likely that the person with the unknown diagnosis has Alzheimer's or is healthy. Comparisons could also be made to other groups, e.g. one with people who have Major Depressive Disorder, or any other disorder or individual attribute.

Figure 4:
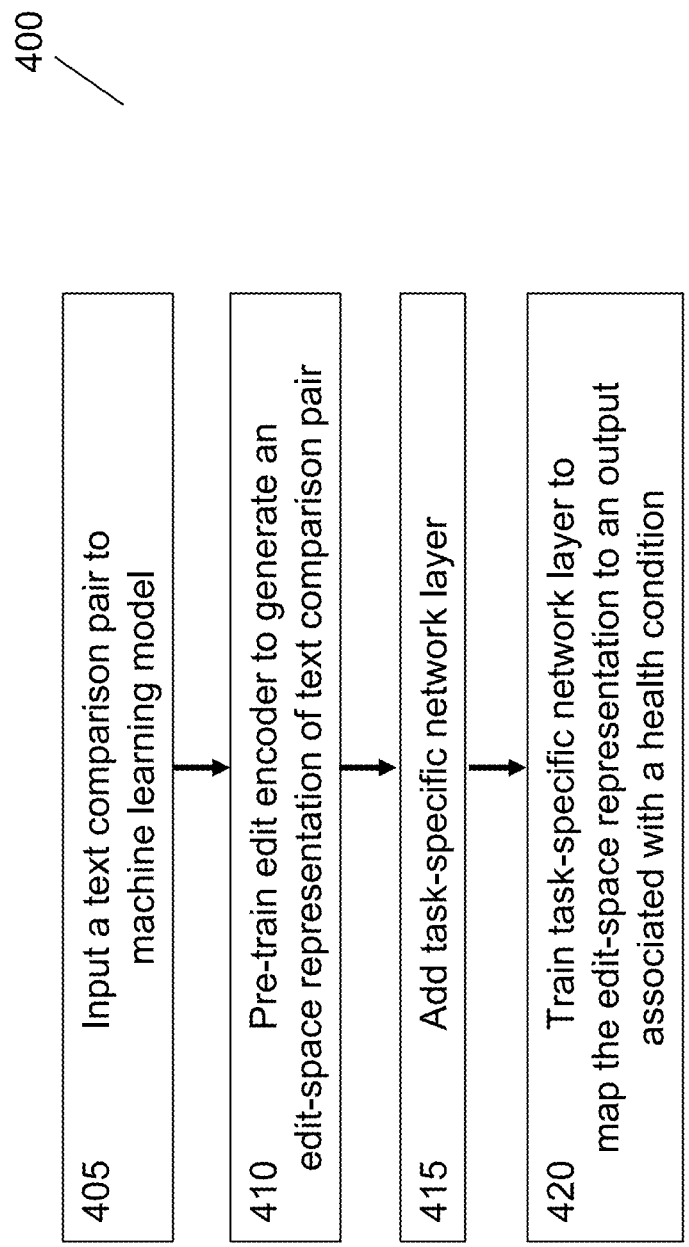
FIG. 4 is a flowchart illustrating a method for pre-training a machine learning model according to the present invention.

FIG. 4 sets out a method 400 for pre-training a machine learning model to evaluate the similarity of a candidate text to a reference text. Method 400 can be performed by the network architecture of FIG. 1.

In step 405 a text comparison pair is input to the machine learning model, where the text comparison pair comprises a reference text and a candidate text, each comprising data encoding a text sequence.

In step 410 an edit encoder of the model architecture is pre-trained such that the edit encoder learns to generate an edit-space representation of the text comparison pair. The edit-space representation encodes information for mapping the reference text to the candidate text. The edit encoder comprises a machine learning encoder model.

Method 400 then performs task-specific training by adding a task-specific network layer in step 415, and in step 420 the machine learning model is trained by mapping the edit-space representation generated by the pre-trained edit encoder to an output associated with a health condition.

Figure 5:
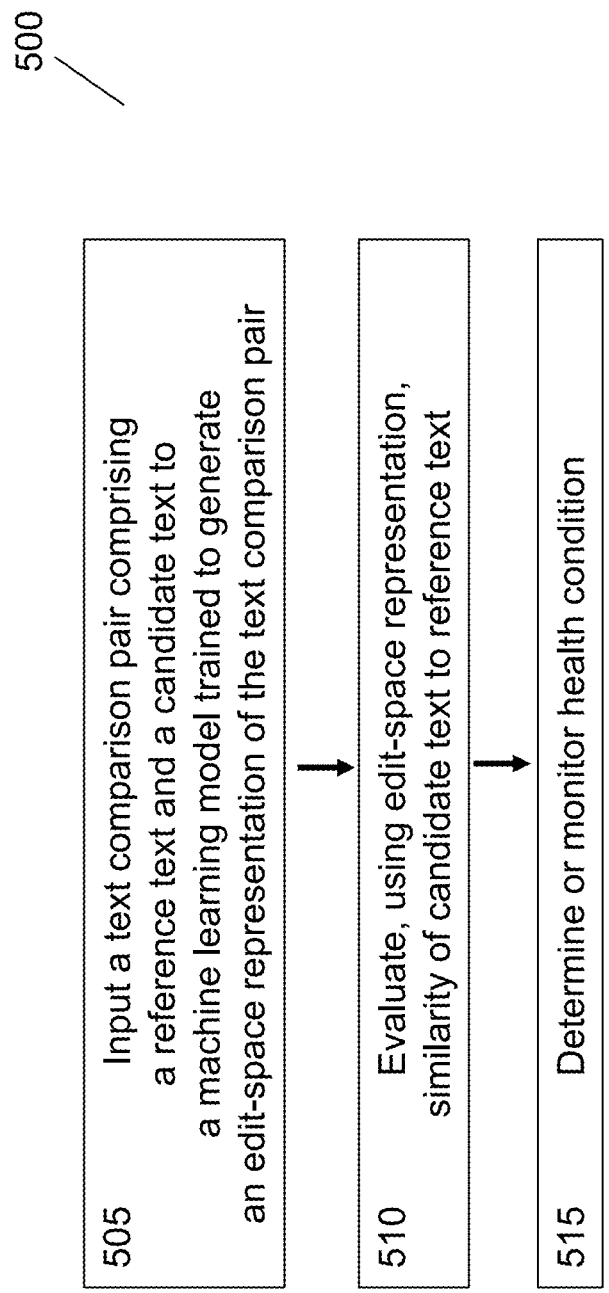
FIG. 5 is a flowchart illustrating a method for monitoring or determining a health condition according to the present invention.

FIG. 5 sets out a method 500 for determining or monitoring a health in a flowchart illustrating a method for monitoring or determining a health condition according to the present invention. Method 500 can be performed by the network architecture of FIG. 2. In step 505 a text comparison pair is input to the machine learning model, where the text comparison pair comprises a reference text and a candidate text, each comprising data encoding a text sequence. The machine learning model comprises an edit encoder trained to generate an edit-space representation that encodes information for mapping the candidate text to the reference text (i.e. using the method of FIG. 4).

In step 510 the edit-space representation is used to evaluate the similarity of the candidate text to the reference text, so as to determine or monitor a health condition at step 515.

Example of Specific Implementation of Model and Results Data

In the below section, a specific implementation of a model architecture (referred to as "ParaBLEU") and the training parameters are described. Results data relating to the ability of the model to predict a human-derived measure of the similarity of two texts is presented. A model trained in this way find application in a wide range of clinical tasks where assessment of the similarity of a speech transcript from a subject to a reference task is required, for example memory recall tasks or tasks relating to the description of a picture or object.

WMT Metrics Shared Task

The WMT Metrics Shared Task is an annual benchmark for automated evaluation metrics for translation systems, where the goal is to predict average human ratings comparing the machine translated candidate x̂ with human-translated reference x, both of which have been translated from the same source sentence.

For the dataset, an identical setup to Bleurt is used [Thibault Sellam et al "Bleurt: Learning robust metrics for text generation" arXiv preprint arXiv:2004.04696, 2020] and Bertscore [Tianyi Zhang et al, "Bertscore: new evaluation metrics for nlg" arXiv preprint arXiv:1707.06875, 2017], where we use the subset of data for which the candidate and reference are in English (where in this case the candidate is a machine translation of a text and the reference a human translation of a text), which we will refer to as the to—English subset. The source (i.e. the original text which is translated), which is unused, can be in any non-English language, the set of which varies from year-to-year. We produce results for the WMT Metrics Shared Task 2017 (WMT17) using the official test, and train on the to—English subsets of WMT15 and WMT16. The training sets contains 5,360 examples.

We report the agreement between ParaBLEU and human scores using two related correlation coefficients: absolute Kendall |T| and absolute Pearson |r|, the latter of which was the official metric of the 2017 task. In our summary results in the main paper, we average these metrics across all source languages but not over reference/candidate language.

ParaCorpus

In addition to our design choices, we also encourage a robust and generalizable pretraining by using a dataset covers a variety of styles and lengths. We collate a number of paraphrase datasets to create a single pretraining dataset we call ParaCorpus, with a total of ~5.1 m examples. All examples have reference and candidate texts and around one third additionally have binary entailment labels. Where the source dataset included three-way labels 'entailment'/'contradiction'/'neutral', 'entailment' was mapped to 1 and the others to 0. A subset of ParaNMT-50M [John Wieting and Kevin Gimpel, "Paranmt-50m: Pushing the limits of paraphrastic sentence embeddings with millions of machine translations" arXiv preprint arXiv:1711.05732, 2017], which includes noisier, speech-like examples, was included for two reasons: to add additional stylistic diversity to the dataset, and to increase the population of the dataset with combined token lengths above 128, which we hypothesize will make the model more robust to the longer examples seen in the WMT datasets.

EXPERIMENTS

In this section, results on WMT17 are presented, benchmarked against the current state-of-the-art approach, along with widely used neural, n-gram and edit-distance-based metrics. We study ParaBLEU performance as a function of number of pretraining steps and the size of the fine-tuning dataset.

Results are for both $ParaBLEU_{base}$, based on $RoBERTa_{base}$ (12 layers, 768 hidden units, 12 heads), and the default model $ParaBLEU_{large}$, based on $RoBERTa_{large}$ (24 layers, 1,024 hidden units, 16 heads). Both models are trained near-identically for 4 epochs on ParaCorpus. Exemplary pretraining hyperparameters details are as follows:

The below table shows the hyperparameters used for the ParaBLEUbase and ParaBLEUlarge models during pretraining, $\alpha$ and $\beta$ are the loss weights from Equation 1.

| Hyperparameter | ParaBLEU$_{base}$ | ParaBLEU$_{large}$ |
|---|---|---|
| Edit encoder base model | RoBERTa$_{base}$ | RoBERTa$_{large}$ |
| Sequence-to-sequence base model | BART$_{base}$ | BART$_{base}$ |
| Batch size (per GPU; examples) | 64 | 32 |
| Batch size (per GPU; max tokens) | 16,384 | 8,192 |
| Learning rate (per GPU) | 4e−4 | 1e−4 |
| Warmup steps | 1,200 | 2,400 |
| Train length (updates) | 20k | 40k |
| Train length (epochs) | 4 | 1 |
| Gradient accumulation steps | 1 | 2 |
| α | 2.0 | 2.0 |
| β | 10.0 | 10.0 |

Pretraining hyperparameters for the ParaBLEUbase and ParaBLEUlarge models used in this paper. These were adapted for a larger architecture from RoBERTa [Yinhan Liu et al, "Roberta: A robustly optimized bert pretraining approach" arXiv preprint arXiv:1907.11692, 2019] and not subject to tuning.

For fine-tuning, we use a batch size of 32, a learning rate of 1 e−5 and train for 40k steps, with a validation set size of 10% (unless otherwise stated).

No reference texts are shared between the train and validation sets, following Bleurt [Thibault Sellam et al, "Bleurt: Learning robust metrics for text generation" arXiv preprint arXiv:2004.04696, 2020]. Pretraining ParaBLEU$_{large}$ takes 10 h on a 16 A100 GPU machine. Fine-tuning takes 8 h on a single A100 GPU machine.

Results

ParaBLEU results on WMT17 are given in the below table, along with a number of baselines. The metrics reported are absolute Kendall |τ| and Pearson |r| averaged across each source language

| Model | |τ| | |r| |
|---|---|---|
| BLEU | 0.292 | 0.423 |
| TER | 0.352 | 0.475 |
| ROUGE | 0.354 | 0.518 |
| METEOR | 0.301 | 0.443 |
| chrF++ | 0.396 | 0.578 |
| BLEURT-large | 0.625 | 0.818 |
| BERTScore-RoBERTa$_{large}$ | 0.567 | 0.759 |
| BERTScore-T5$_{large}$ | 0.536 | 0.738 |
| BERTScore-DeBERTa$_{large}$ | 0.580 | 0.773 |
| MoverScore | 0.322 | 0.454 |
| ParaBLEU$_{large}$ | 0.653 | 0.843 |
| ParaBLEU$_{base}$ | 0.589 | 0.785 |

Baselines include BLEURT, a BERT-based learnt metric that is pretrained to predict a number of existing text similarity metrics, along with BERTScore, a non-learned neural metric that uses a matching algorithm on top of neural word embeddings, similar to n-gram matching approaches. MoverScore [Wei Zhao et al, "Moverscore: Text generation evaluating with contextualized embeddings and earth mover distance" arXiv preprint arXiv:1909.02622, 2019] is similar to BERTScore, but uses an optimal transport algorithm. BLEU, ROUGE, METEOR and chrF++ are widely used n-gram-based methods, working at the word, subword or character level. TER is an edit-distance-based metric, similar to WER (word error rate).

ParaBLEUlarge achieves new state-of-the-art results on WMT17, exceeding the previous state-of-the-art approach, BLEURT, on both correlation metrics. We note that non-neural metrics perform the worst, of which the character-level n-gram-matching algorithm chrF++ performs the best. Non learned neural metrics (BERTScore and MoverScore) tend to perform better, and learned neural metrics (BLEURT and ParaBLEU) perform the best. BLEU, the most widely used metric, has the poorest correlation with human judgements. This is consistent with results seen previously in the literature [Tianyi Zhang et al, "Bertscore: Evaluating text generation with bert" arXiv preprint arXiv:1904.09675, 2019] [Thibault Sellam et al, "Bleurt: Learning robust metrics for text generation" arXiv preprint arXiv: 2004.04696, 2020]. The significant drop in performance from ParaBLEU$_{large}$ to ParaBLEU$_{base}$ highlights the benefit of larger, more expressive pretrained language models.

The invention claimed is:

1. A computer implemented method of training a machine learning model to evaluate the similarity of a candidate text to a reference text for determining or monitoring a health condition, where the machine learning model takes as input a text comparison pair, where a text comparison pair comprises the reference text and the candidate text, each comprising data encoding a text sequence, the method comprising:
   pre-training an edit encoder such that it learns to generate an edit-space representation of an input text comparison pair, where the edit-space representation encodes information for mapping the reference text to the candidate text, the edit encoder comprising a machine learning model; and
   performing task-specific training by adding a task-specific network layer and training the task-specific network layer to map the edit-space representation generated by the pre-trained edit encoder to an output associated with a health condition,
   wherein pre-training the edit encoder comprises at least one of generative conditioning or masked language modelling,
   wherein generative conditioning comprises:
   connecting the edit encoder to a sequence-to-sequence encoder-decoder suitable for mapping an input reference text to an output candidate text, where the edit encoder is connected such that the sequence-to-sequence encoder-decoder is conditioned using the edit-space representation generated by the edit encoder;
   inputting the text comparison pair into the edit encoder and inputting the reference text of the text comparison pair into the sequence-to-sequence encoder-decoder; and
   training the edit encoder and sequence-to-sequence encoder-decoder together to map the inputs to the candidate text of the text comparison pair output by the sequence-to-sequence decoder, such that the edit encoder learns to generate the edit-space representation usable by the sequence-to-sequence encoder-decoder to generate the candidate text based on the input reference text, and
   wherein masked language modelling comprises:
   providing a linear projection layer after the edit encoder;
   inputting the text comparison pair into the edit encoder where part of the input text-comparison pair is withheld; and
   training the edit encoder and the linear projection layer together to predict the withheld part of the input text-comparison pair.

2. The computer implemented method of claim 1 wherein an information bottleneck is provided between the edit encoder and the sequence-to-sequence encoder-decoder such that the candidate text cannot be passed in full from the edit encoder to the sequence-to-sequence encoder-decoder during training.

3. The computer implemented method of claim 1 wherein pre-training additionally comprises entailment training using an entailment data set comprising text comparison pairs with an entailment label indicating whether the reference text logically entails the candidate text, the method comprising:
adding an entailment projection layer after the edit encoder, the entailment projection layer trainable to predict the entailment label using the edit-space representation provided by the edit encoder;
training the edit encoder and entailment projection layer to map an input text comparison pair to the entailment label.

4. The computer implemented method of claim 1 wherein performing task-specific training comprises:
training the task-specific network layer using a task-specific data set comprising labelled text comparison pairs, where the labelled text comparison pairs are input into the edit encoder and the task-specific layer is trained to predict the label.

5. The computer implemented method of claim 4 wherein performing task-specific training comprises:
fixing the weights of one or more layers of the edit encoder after pre-training, inputting a labelled text-comparison pair and training only the task-specific network layer to map the edit-space representation generated by the edit encoder; or
training the edit encoder and the task-specific layer together such that the edit encoder learns further modified edit-space representations optimised for a specific task.

6. The computer implemented method of claim 4 wherein the task-specific data set comprises labelled text comparison pairs, each comprising a label associated with at least one of:
a human-derived measure of the similarity of the text comparison pair; or
an output associated with a health condition of the speaker of the candidate text.

7. The computer implemented method of claim 6 wherein the task-specific data set comprises text comparison pairs, each comprising a label associated with a health condition of the speaker of the candidate text, where the health condition comprises one or more of: a neurodegenerative disease, neurobehavioral condition, head injury, stroke, or psychiatric condition.

8. The computer implemented method of claim 1 wherein the task-specific layer comprises one or both of: a classification layer, a regression layer.

9. The computer implemented method of claim 1 comprising, prior to pre-training, initialising the edit encoder weights by performing initialisation training, where initialisation training comprises unsupervised training on unlabelled text data.

10. The computer implemented method of claim 1 wherein a text comparison pair comprises a data sequence comprising a candidate text and a concatenated reference text.

11. The computer implemented method of claim 1 wherein each reference text and each candidate text comprises a sequence of text tokens, each text token encoding a sub-word, word or multiple word sequence.

12. The computer implemented method of claim 1 wherein the edit encoder comprises a Transformer encoder.

13. A computer implemented method of using a machine learning model to evaluate the similarity of a candidate text to a reference text to determine or monitor a health condition, where the machine learning model takes as input a text comparison pair, where the text comparison pair comprises the reference text and the candidate text, each comprising data encoding a text sequence, the method comprising:
inputting the text comparison pair into a trained machine learning model, the machine learning model comprising an edit encoder trained to generate an edit-space representation that encodes information for mapping the candidate text to the reference text, the training comprising at least one of generative conditioning or masked language modelling,
the generative conditioning comprising:
connecting the edit encoder to a sequence-to-sequence encoder-decoder suitable for mapping to an output candidate text, where the edit encoder is connected such that the sequence-to-sequence encoder-decoder is conditioned using the edit-space representation generated by the edit encoder;
inputting the text comparison pair into the edit encoder and inputting the reference text of the text comparison pair into the sequence-to-sequence encoder-decoder; and
training the edit encoder and sequence-to-sequence encoder-decoder together to map the inputs to the candidate text of the text comparison pair output by the sequence-to-sequence decoder, such that the edit encoder learns to generate the edit-space representation usable by the sequence-to-sequence encoder-decoder to generate the candidate text based on an input reference text, and
the masked language modelling comprising:
providing a linear projection layer after the edit encoder;
inputting the text comparison pair into the edit encoder where part of the input text-comparison pair is withheld; and
training the edit encoder and the linear projection layer together to predict the withheld part of the input text-comparison pair;
using the edit-space representation to evaluate the similarity of the candidate text to the reference text to determine or monitor a health condition.

14. The computer implemented method of claim 13 wherein the candidate text encodes text data corresponding to a transcript of speech from a subject, the method comprising using the edit-space representation to determine or monitor a health condition of the subject.

15. The computer implemented method of claim 13, wherein using the edit-space representation to evaluate the similarity of the candidate text to the reference text to determine or monitor a health condition comprises:
comparing the edit-space representation of a text comparison pair from a test subject with an edit-space representation of a text comparison pair from a healthy subject and/or a subject with a health condition.

16. The computer implemented method of claim 13, where the machine learning model comprises a linear projection layer for mapping the edit-space representation generated by the edit encoder to an output associated with a health condition prediction and wherein using the edit-space representation to evaluate the similarity of the candidate text to the reference text to determine or monitor a health condition comprises:

inputting a text comparison pair from a test subject into the machine learning model to provide a health condition prediction.

17. The computer implemented method of claim 13 wherein the machine learning model is further trained by:
performing task-specific training by adding a task-specific network layer and training the task-specific network layer to map the edit-space representation generated by the edit encoder to an output associated with a health condition.

18. A system for evaluating the similarity of a candidate text to a reference text to determine or monitor a health condition, the system comprising a processor configured to:
receive a text comparison pair, where the text comparison pair comprises the reference text and the candidate text, each comprising data encoding a text sequence;
providing a health condition prediction by inputting inputting the text comparison pair into a trained machine learning model, the machine learning model comprising an edit encoder trained to generate an edit-space representation that encodes information for mapping the candidate text to the reference text, the training comprising at least one of generative conditioning or masked language modelling,
the generative conditioning comprising:
connecting the edit encoder to a sequence-to-sequence encoder-decoder suitable for mapping an input reference text to an output candidate text, where the edit encoder is connected such that the sequence-to-sequence encoder-decoder is conditioned using the edit-space representation generated by the edit encoder;
inputting the text comparison pair into the edit encoder and inputting the reference text of the text comparison pair into the sequence-to-sequence encoder-decoder; and
training the edit encoder and sequence-to-sequence encoder-decoder together to map the inputs to the candidate text of the text comparison pair output by the sequence-to-sequence decoder, such that the edit encoder learns to generate the edit-space representation usable by the sequence-to-sequence encoder-decoder to generate the candidate text based on the input reference text, and
the masked language modelling comprising:
providing a linear projection layer after the edit encoder;
inputting the text comparison pair into the edit encoder where part of the input text-comparison pair is withheld; and
training the edit encoder and the linear projection layer together to predict the withheld part of the input text-comparison pair; and
wherein the machine learning model comprises a linear projection layer trained to map the edit-space representation generated by the edit encoder to an output associated with a health condition prediction.

* * * * *